United States Patent [19]

Johnstone

[11] Patent Number: 5,675,042
[45] Date of Patent: Oct. 7, 1997

[54] SELECTIVE HYDROXYLATION OF PHENOL OR PHENOLIC ETHERS

[75] Inventor: Robert Alexander Walker Johnstone, Wirral, United Kingdom

[73] Assignee: Solvay Interox Limited, Cheshire, United Kingdom

[21] Appl. No.: 448,530

[22] PCT Filed: Dec. 9, 1993

[86] PCT No.: PCT/GB93/02519

§ 371 Date: Aug. 3, 1995

§ 102(e) Date: Aug. 3, 1995

[87] PCT Pub. No.: WO94/14740

PCT Pub. Date: Jul. 7, 1994

[30] Foreign Application Priority Data

Dec. 19, 1992 [GB] United Kingdom ............... 9226494

[51] Int. Cl.[6] ................ C07C 41/04; C07C 43/20
[52] U.S. Cl. ................ 568/650; 568/763; 568/771
[58] Field of Search ............... 560/650, 763, 560/771

[56] References Cited

U.S. PATENT DOCUMENTS

| 4,847,437 | 7/1989 | Wu ........................ 568/763 X |
| 5,387,724 | 2/1995 | Johnstone et al. ........... 568/771 |
| 5,426,244 | 6/1995 | Sugai et al. ............... 568/771 |

*Primary Examiner*—Paul F. Shaver
*Attorney, Agent, or Firm*—Lar and Taylor

[57] ABSTRACT

Phenols, and related aromatic compounds, phenolic ethers, can be hydroxylated selectively using hydrogen peroxide in the presence of an amorphous or crystalline tin or cerium phosphate catalyst in a solvent containing an aliphatic carboxylic acid. The process is particularly suitable for phenol itself, and advantageously employs a catalyst obtained by heating an hydrated amorphous or crystalline tin or cerium phosphate for example at about 100° C. A convenient hydroxylation temperature is in the range of 50° to 90° C., and a convenient solvent is acetic acid.

18 Claims, No Drawings

SELECTIVE HYDROXYLATION OF PHENOL OR PHENOLIC ETHERS

The present invention relates to a process for hydroxylating phenols and more particularly to a process in which phenols are hydroxylated using hydrogen peroxide in the presence of a catalyst.

Phenol is a readily available raw material which can be hydroxylated using aqueous hydrogen peroxide and a catalyst to produce dihydric phenols, and particularly mixtures containing hydroquinone and catechol. However, the introduction of a second hydroxyl substituent onto the aromatic nucleus tends to activate the molecule towards further reaction and this leads to the formation of a mixture of unwanted tarry by-products. Self-evidently it would be desirable to hydroxylate selectively, i.e. favour dihydric phenol formation compared with tarry by-product formation.

A commercial process has been developed for hydroxylating phenol based upon catalysed hydrogen peroxide which tends to produce mixtures containing a major fraction of catechol, but additionally a minor, significant fraction of hydroquinone, typically in a mole ratio of about 3:1. The proportion of tarry by-products has been controlled by limiting very strictly to the use of very low mole ratios of hydrogen peroxide to phenol, but inevitably this restricts the extent of conversion of the phenol and leads to the recycling of an overwhelming fraction of unreacted phenol which in turn reduces the space yield of the plant. It would be desirable to develop a process which enabled a higher proportion of the phenol to be reacted to the desired end-products in each cycle.

In the course of the studies leading to the present invention, a range of metal catalysts have been tested for the hydroxylation of phenols with varying levels of success and failure, demonstrating that catalysts useful for other hydrogen peroxide reactions cannot necessarily be transferred to phenol hydroxylation with a guarantee of success.

It is an object of the present invention to ameliorate or overcome one or more of the difficulties indicated herein with regard to known processes for the catalysed hydroxylation of phenol.

According to the present invention, there is provided a process for the hydroxylation of a substrate comprising a phenol or related aromatic compounds by reaction with hydrogen peroxide in the presence of a catalyst, characterised in that the substrate is a phenol or phenolic ether and the reaction is carried out in a solvent containing an effective amount of an aliphatic carboxylic acid and the catalyst comprises one or both of tin (IV) or cerium (IV) phosphate.

By the use of a process according to the present invention, it is possible to obtain good selectivity of reaction towards the introduction of a single additional hydroxyl substituent round the aromatic nucleus of the substrate, normally ortho or para to the existing substituent.

The substrate can be mono, bi or poly-nuclear and, preferably, is mono-nuclear. The nucleus or nuclei is or are particularly suitably carbocyclic. The most preferred nucleus is benzene. Although the substrate may contain more than one of the relevant substituents namely hydroxyl or ether, it is preferable for only one to be present. A particularly preferred substrate comprises phenol itself. The substrate nucleus may be further substituted, if desired, for example by an alkyl group, $R_a$, preferably short chain such as methyl or ethyl. When the substituent is an ether, suitably of formula —$OR_b$, $R_b$ is suitably alkyl and preferably short chain alkyl such as methyl or ethyl.

The catalyst employed in processes of the present invention comprises an amorphous or crystalline tin (IV) or cerium (IV) phosphate. The catalyst can be prepared by the reaction between a tin or cerium salt such as especially the chloride or the sulphate and phosphoric acid, producing a solid metal phosphate precipitate. The reaction can conveniently by conducted at, or around ambient temperature. The extent of crystallinity can be controlled by controlling the length of time that the precipitate remains in contact with its supernatant liquor, ie aging. An initially amorphous precipitate becomes increasingly crystalline as the aging period lengthens. For convenience, the reaction period including aging time is often selected in the range of from about 10 minutes to about 2 hours, and particularly about 30 to 60 minutes. When this method is employed, it is preferable that the mole ratio of tin or cerium salt to phosphoric acid is approximately stoichiometric to avoid chemical waste and minimise contamination of the product with unreacted starting material.

The catalyst may alternatively be made by an analogous process to that described by A. Clearfield and D. S. Thakur in Applied Catalysis, 26, 1 (1986), by substituting the corresponding tin or cerium compound for the zirconium compound.

Preferably the catalyst is dried or at least partially dehydrated before it is employed. Drying and/or dehydration can be effected conveniently by heating the material, suitably in an oven. A convenient temperature range extends up to about 500° C. such as from about 50° to about 300° C. After drying, the solid catalyst tends to adopt an agglomerated or aggregated form and is preferably disintegrated into smaller particles, such as by washing with water and then re-drying.

The amount of catalyst to employ is, at least to some extent, at the discretion of the operator. In conjunction with the solvent system described hereinafter, the catalyst is substantially insoluble. Accordingly, it can be readily separated from the reaction mixture and re-used. It is often convenient to employ from 1 to 25 parts w/w of catalyst per 100 parts of substrate.

The solvent system employed in the present invention process contains essentially an aliphatic carboxylic acid. Conveniently, an aqueous solution containing at least 15% v/v carboxylic acid may be employed, and preferably at least 80% v/v. The carboxylic acid preferably contains from 1 to 6 carbon atoms and is, especially suitably, acetic acid.

The amount of hydrogen peroxide to employ is at the discretion of the user. To some extent, the selectivity of the reaction is better when a comparatively low mole ratio of hydrogen peroxide to substrate is employed, but the conversion of the substrate, e.g. phenol, is lower so that a higher proportion remains for processing subsequently. On the other hand if a higher mole ratio of hydrogen peroxide to substrate is employed, the conversion of substrate is higher, but the selectivity tends to be impaired. The mole ratio of hydrogen peroxide:substrate in the reaction mixture is often selected in the range of 0.05:1 to 2:1, and in many instances from about 0.1:1 to about 1:1. Most acceptable results have been obtained in the region of about 0.2:1 to about 0.6:1.

The hydrogen peroxide can be introduced into the reaction mixture in a variety of different ways. In one way, it can all be introduced in a single shot, though for safety's sake it preferably takes from 5 to 15 minutes. In a second way, it can be introduced incrementally, in for example from 2 to 25 increments. In a third way it can be introduced continuously. Its period of introduction may extend to the entire reaction period, if desired. It is most convenient to employ concentrated hydrogen peroxide, of for example from 30 to 75% w/w.

The reaction is suitably conducted at an elevated temperature, that most conveniently is selected in the range of from 45° to 95° C., and especially from 50° to 90° C. It will be recognised that there is a tendency for greater selectivity towards hydroxylation at lower reaction temperatures and a tendency towards a higher reaction rate at higher temperatures within the aforementioned range. Particularly desirable selectivities have been obtained in the temperature range of about 55° to about 60° C. The reaction is preferably permitted to continue until all the hydrogen peroxide has been consumed. The overall reaction period will depend upon the interaction of tat least three factors, namely the reaction temperature, mole ratio of $H_2O_2$:substrate and nature of the substrate. For an equimolar reaction, the reaction period often lies within the range of 3 to 12 hours, and to a first approximation, a pro rata period can be employed for other mole ratios, though in many embodiments the reaction is permitted to last for a period of from about 4 to about 6 hours, irrespective of the mole ratio employed.

At the end of the reaction period, the solid particulate catalyst can be recovered by conventional separation methods, including filtration and centrifugation. The solvent, substrate and reaction products may be separated by conventional distillation or fractionation techniques. The recovered substrate and solvent can be recycled so as to maximise the overall conversion of substrate to products and minimise solvent costs.

Having described the present invention in general terms, specific embodiments thereof will now be described in greater detail by way of example only.

EXAMPLES 1 TO 6

The catalyst employed in these Examples was made as follows:

Tin phosphate was made by reaction 111.2 ml of a 104.2 g/l aqueous solution of $SnCl_4.5H_2O$ with 108 ml of a 54.2 g/l aqueous solution of $H_3PO_4$ for 30 minutes at room temperature. The product was washed with demineralised water until the pH of the washings reached 3 to 4, and then dried at 50° C. The dried product was then disintegrated in water at room temperature, filtered off, water washed until the pH of the washings reached pH 4 to 5, and then dried at 110° C.

In each of Examples 1 to 6, phenol (9.4 g, 0.1 mol) was dissolved in acetic acid (50 ml), particulate catalyst (0.5 g) was introduced and the mixture heated to the desired temperature. Aqueous hydrogen peroxide having the selected concentration (0.05 mol) was introduced with stirring over about an hour and the reaction mixture was maintained at temperature for a further 5 hours. The cooled reaction mixture was stored in a tared bottle.

For analysis, a carefully weighed sample of about 0.25 g was diluted to 50 ml with methanol and 20 μl was injected into an HPLC, $C_{18}$ column and compared with a standard solution containing hydroquinone, 10 mg, catechol, 10 mg, and phenol, 30 mg, in 50 ml of methanol. The solvent mixture/gradient system was:

System A—2% acetic acid in acetonitrile;

System B—2% aqueous acetic acid;

10% A/90% B on injection of sample altered progressively to 50% A/50% B over 10 minutes.

The eluent was analysed at 280 nm using a diode array detector.

The results for the various temperatures and concentrations of hydrogen peroxide are summarised in Table 1 below.

The term % selectivity herein indicates the molar proportion of the specified product on the basis of all products and by-products. Para herein indicates hydroquinone, ortho indicates catechol and total indicates the combined proportions of the two desired products, viz hydroquinone and catechol.

TABLE 1

| Ex. No. | Temp °C. | % w/w $H_2O_2$ | % phenol converted | % Selectivity para | ortho | total |
|---|---|---|---|---|---|---|
| 1 | 70 | 30 | 26.5 | 22.6 | 34.7 | 57.3 |
| 2 | 70 | 35 | 37.8 | 12.7 | 15.6 | 28.3 |
| 3 | 60 | 40 | 28.2 | 24.8 | 42.9 | 67.7 |
| 4 | 60 | 35 | 17.1 | 30.9 | 46.8 | 77.7 |
| 5 | 50 | 35 | 18.2 | 28.6 | 41.2 | 69.8 |
| 6 | 50 | 45 | 19.6 | 19.4 | 30.6 | 50.0 |

EXAMPLES 7 TO 9

In Examples 7 to 9 the catalyst was prepared using a further batch of the same solutions as for Examples 1 to 6, except that the reaction was carried out for 1.5 hours, and solid product obtained by rotary evaporation to dryness of the reaction liquors. The solid produced was then ground using a pestle and mortar to produce a free flowing powder.

The hydroxylation reaction used the reagent quantities and conditions for example 4, except that an addition time of 45 minutes, was employed in all cases. In Example 8, propionic acid was employed in place of acetic acid, and in Example 9, anisole was used in place of phenol, and the temperature was maintained for 6 hours. The results are summarised in Table 2 below.

TABLE 2

| Ex. No. | % phenol converted | % Selectivity para | ortho | total |
|---|---|---|---|---|
| 7 | 25.8 | 24.6 | 33.8 | 58.4 |
| 8 | 31.5 | 7.6 | 18.8 | 26.4 |
| 9 | 48.3 | 4.4 | 9.3 | 13.7 |

EXAMPLES 10 TO 12

The catalyst in examples 10 to 12 was prepared by the method employed in Examples 1 to 6 above, except that ceric chloride was employed instead of tin chloride. Hydroxylation reactions of phenol were carried out using the same conditions as for Examples 4 above, except that varying amounts of catalyst and $H_2O_2$ were used, as stated in Table 3 below. The results are summarised in Table 3.

TABLE 3

| Ex. No. | catalyst g | moles $H_2O_2$ | % phenol converted | % Selectivity para | ortho | total |
|---|---|---|---|---|---|---|
| 10 | 0.5 | 0.05 | 16.8 | 31.0 | 63.8 | 94.8 |
| 11 | 1.0 | 0.1 | 27.7 | 26.4 | 52.7 | 79.1 |
| 12 | 2.0 | 0.15 | 33.7 | 27.0 | 37.4 | 64.4 |

I claim:

1. A process for the hydroxylation of a substrate comprising a phenol or related aromatic compound by reaction with hydrogen peroxide in the presence of a catalyst, wherein the substrate comprises a phenol or phenolic ether, the reaction is carried out in a solvent containing an effective amount of an aliphatic carboxylic acid and the catalyst comprises one or both of tin (IV) or cerium (IV) phosphate.

2. A process according to claim 1 wherein the substrate is mono-nuclear.

3. A process according to claim 2 wherein the substrate contains a benzene nucleus substituted by a single hydroxyl or ether.

4. A process according to claim 3 wherein the substrate comprises phenol.

5. A process according to any preceding claim wherein the catalyst employed therein is obtained by reacting tin or cerium chloride or sulphate with phosphoric acid.

6. A process according to claim 5 wherein the tin or cerium phosphate catalyst is at least partially dehydrated before use.

7. A process according to claim 1 wherein the catalyst is employed in an amount of from 1 to 25 parts w/w per 100 parts of aromatic compound.

8. A process according to claim 1 wherein the carboxylic acid contains from 1 to 6 atoms.

9. A process according to claim 8 wherein the carboxylic acid comprises acetic acid.

10. A process according to claim 1 wherein the solvent comprises an aqueous solution containing at least 20% w/w of an aliphatic carboxylic acid.

11. A process according to claim 10 wherein the concentration of carboxylic acid is at least 15% v/v.

12. A process according to claim 1 wherein the hydroxylation reaction is conducted at a temperature of from 45° to 95° C.

13. A process according to claim 1 wherein the hydroxylation reaction employs hydrogen peroxide in a mole ratio to aromatic compound in the range of from 0.05:1 to 2:1.

14. A process according to claim 2 wherein the substrate contains a benzene nucleus.

15. A process according to claim 5 wherein the catalyst is dried before use.

16. A process according to claim 13 wherein said mole ratio is from 0.1:1 to about 1:1.

17. A process according to claim 1 wherein the solvent comprises an aqueous solution containing at least 20% w/w of acetic acid, wherein said catalyst comprises an at least partially dehydrated cerium or tin phosphate catalyst present in an amount of from 1 to 25 parts w/w per 100 parts of substrate, and wherein the reaction is carried out at a temperature of from 45°–90° C. and with a hydrogen peroxide:substrate mole ratio of from 0.05:1 to 2:1.

18. A process according to claim 17 wherein said substrate comprises phenol.

\* \* \* \* \*